(12) United States Patent
Sparling, II et al.

(10) Patent No.: US 9,782,354 B2
(45) Date of Patent: Oct. 10, 2017

(54) ENTERIC ACTIVE SUBSTANCE DELIVERY

(76) Inventors: Grant Rufus Sparling, II, Blyth (CA); Taha Basim Al-Jishi, Qatif (SA); Vishal Prasanth Babu, Waterloo (CA); Sondus Mohammad Towfik Bellow, Rochester, NY (US); Somee Park, Winipeg (CA); Krisha Jay Patel, Windsor (CA); Rod Rodjanapiches, Bangkok (TH); Vigne Sridharan, Rockwood (CA); Lisa Tang, Ottawa (CA); Rameez Moez Badrudin Visram Virji, Calgary (CA); Qihui (Jessica) Zhu, Brossard (CA)

( * ) Notice: Subject to any disclaimer, the term of this patent is extended or adjusted under 35 U.S.C. 154(b) by 0 days.

(21) Appl. No.: 13/818,319

(22) PCT Filed: Jul. 20, 2011
(Under 37 CFR 1.47)

(86) PCT No.: PCT/CA2011/000835
§ 371 (c)(1),
(2), (4) Date: Oct. 31, 2013

(87) PCT Pub. No.: WO2012/024767
PCT Pub. Date: Mar. 1, 2012

(65) Prior Publication Data
US 2014/0199389 A1 Jul. 17, 2014

Related U.S. Application Data

(60) Provisional application No. 61/376,950, filed on Aug. 25, 2010.

(51) Int. Cl.
*A61K 9/48* (2006.01)
*A61K 39/00* (2006.01)
*A61K 39/145* (2006.01)
*A61K 38/28* (2006.01)
*C12N 7/00* (2006.01)
*A61K 39/12* (2006.01)

(52) U.S. Cl.
CPC .............. *A61K 9/4816* (2013.01); *A61K 9/48* (2013.01); *A61K 38/28* (2013.01); *A61K 39/12* (2013.01); *A61K 39/145* (2013.01); *C12N 7/00* (2013.01); *A61K 39/00* (2013.01); *C12N 2760/16134* (2013.01)

(58) Field of Classification Search
None
See application file for complete search history.

(56) References Cited

U.S. PATENT DOCUMENTS

| 4,138,013 | A | | 2/1979 | Okajima | |
|---|---|---|---|---|---|
| 6,126,767 | A | * | 10/2000 | Smith | A61J 3/005 156/308.8 |
| 6,309,666 | B1 | * | 10/2001 | Hatano et al. | 424/463 |
| 7,097,851 | B1 | * | 8/2006 | Takada | 424/435 |
| 2003/0077297 | A1 | * | 4/2003 | Chen et al. | 424/400 |
| 2007/0065502 | A1 | * | 3/2007 | Baksh | 424/451 |

FOREIGN PATENT DOCUMENTS

| CA | 2181502 A1 | 1/1997 |
|---|---|---|
| CA | 2344680 A1 | 4/2000 |
| CN | 1321085 A | 11/2001 |
| EP | 0112183 A2 | 6/1984 |
| JP | S5352619 A | 5/1978 |
| JP | 2000103732 A | 4/2000 |
| WO | WO 2005123088 A1 * | 12/2005 |
| WO | 2008119943 A2 | 10/2008 |
| WO | WO 2009/050646 A2 * | 4/2009 |

OTHER PUBLICATIONS

"PCT International Search Report and Written Opinion dated Oct. 4, 2011 for PCT/CA2011/000835, from which the instant application is based," 11 pgs.

* cited by examiner

*Primary Examiner* — Patricia Duffy
*Assistant Examiner* — Garen Gotfredson
(74) *Attorney, Agent, or Firm* — Fredrikson & Byron, P.A.

(57) ABSTRACT

An oral enteric delivery system includes an outer shell assembled from multiple solid shell segments joined together by a binder. The binder does not dissolve upon exposure to the gastric environment, but it dissolves in the upper small intestine, causing the shell to disintegrate and causing the payload contained within the shell to be released in the digestive tube downstream of the stomach.

20 Claims, 2 Drawing Sheets

ENTERIC ACTIVE SUBSTANCE DELIVERY

RELATED APPLICATIONS

This application is a 35 U.S.C. 371 national stage filing from International Application No. PCT/CA2011/000835 filed Jul. 20, 2011 and claims priority to U.S. Provisional Patent Application No. 61/376,950 filed Aug. 25, 2010, the teachings of which are incorporated herein by reference.

FIELD OF THE INVENTION

The present invention relates to a method for forming an enteric barrier on a preparation for oral delivery of active substances to the small intestine.

BACKGROUND OF THE INVENTION

Vaccination is an efficient and cost-effective form of preventing infectious diseases. However, most currently available vaccines are delivered by injection, which makes mass immunization more costly and less safe, particularly in resource-poor developing countries. Even in developed countries, patients would overwhelmingly choose to avoid injections if an alternative effective delivery system were available.

The benefits of oral vaccines go beyond just the fear of needles. Oral vaccines have several other attractive features compared with parenteral vaccines. There is always a risk that the hypodermic needle or the point of needle entry might not be properly sterilized, and oral vaccines eliminate this risk. Oral vaccines can retain potency for longer at room temperature, potentially allowing final distribution without refrigeration or at least with reduced need for refrigeration. They are also cheaper to administer because patients do not need administration by trained medical staff in a clinical setting to get their doses of vaccine. The advantages of such vaccines for society at large include faster manufacturing, ease of stockpiling and more rapid distribution to the needy. Oral vaccines can also be cheaper to produce as a result of less stringent regulatory requirements for oral preparations compared with parenteral preparations. Elimination of used needles (a byproduct of the vaccination process) can also alleviate any concerns regarding the unsafe disposal of needles, which is known to be responsible for a number of accidents.

Oral vaccination has received a great deal of attention in recent years. It is known in the art that the small intestine of mammals contains at least one main immune induction site, where antigen is processed and presented for the initiation of an immune response by the host's immune system. Lymphoid tissue associated with the small intestine allows antigen uptake at these sites and the end result is a mucosal immune response, as well as a systemic immune response. This simultaneous induction of both mucosal and systemic immunity against the antigen of interest is a well-recognized additional advantage of oral vaccination, not usually observed with subcutaneous or intramuscular vaccines that normally elicit only a systemic immune response.

Oral vaccination can also prevent some of the dangerous or fatal side-effects allegedly caused by some adjuvants commonly present in the injectable vaccine preparations, such as squalene. Adjuvants which are normally well-tolerated by the body when absorbed through the digestive system can have dangerous and fatal effects (including autoimmune arthritis and lupus) when administered by injection. A further benefit of an oral vaccine's reduced potential for side effects is the increased acceptance of vaccination within certain population groups which currently oppose vaccines on the basis of the perceived potential for harm caused by the adjuvants present in the injectable vaccines.

Also, compared to other non-injection vaccine alternatives (e.g. intranasal mist vaccination), live-viruses in intestinally administered vaccines are not known to travel into the brain and central nervous system—a rare but potentially harmful complication of intranasal vaccination.

However, oral vaccination has been regarded historically as likely to be less effective, since vaccine antigens can easily undergo digestion in the gastro-intestinal tract prior to induction of an immune response. At present, there are a limited number of oral vaccines approved for human use: the well-known polio vaccine (which is administered to infants in a drop form), a Ty21a typhoid vaccine, a cholera vaccine, a malaria vaccine, an adenovirus vaccine discontinued in 1999 (not for safety related reasons), etc. There is a large unmet market need for more oral vaccines for the prevention of infectious diseases.

It remains a challenge for an antigen to be efficiently delivered to the mucosa of the small intestine, not in small part attributable to vaccines' high susceptibility to degradation during gastric residence, due to both acidity and pepsinolytic digestion. The gastric pH is very acidic (typically between about pH 1.5 and 1.9). Under gastric conditions, acid-labile compounds typically degrade and are not readily available for downstream uptake. The protein-digesting enzyme pepsin (normally present in the stomach) will also attack and degrade a vaccine's antigens (which typically consist of fragments of proteins and peptides).

To this end, there is a need for suitable systems to ensure protection of orally-administered immunogenic proteins from the acidic gastric environment.

The prior art response to the problem of pH sensitivity of acid labile drugs that need to be taken orally was to administer them in a dosage form that protects the drug from the acidic gastric environment. The delayed liberation of orally administered drugs has been achieved through a range of formulation approaches, including coatings, capsule devices, osmotic pumps, etc.

Enteric coatings are probably the most widely used method of protecting against gastric degradation. Enteric coating methods typically form a barrier around the active ingredient, with a coating that does not dissolve upon exposure to the low pH of the gastric environment. Such enteric coatings typically dissolve at a pH greater than 6, such as that found in the upper small intestine, causing the active ingredients to be released in an environment where they will not significantly degrade, and therefore can be absorbed.

However, the full-pill enteric coatings known in the art continue to have several drawbacks. There remains uncertainty as to the location at which the enteric coating starts to dissolve. Large inter- and intra-patient variations exist in such parameters as gastro-intestinal motility and pH profile, leading to a lack of control associated with the point of delivery. Some known enteric coating compositions can only be applied through the use of organic solvent-based coating solutions (e.g. acetone or chlorinated solvents) which are undesirable. Other enteric coating methods involve high temperatures of application or curing. Yet other capsules and coatings known in the art contain products derived from dead animals (gelatine) or crustaceans (chitosan), which are objected to by some users.

SUMMARY OF THE INVENTION

It is a major aspect of the present invention to provide an improvement to prior art enteric-coated delivery systems, by providing an enteric delivery system in which the capsule disintegrates more easily and more completely and releases substantially its entire content at a more precise and adjustable point in the intestine.

It is a further aspect of the present invention to provide an oral delivery system having an enteric coating that does not dissolve upon exposure to the gastric environment, but that dissolves in the upper small intestine, causing the active ingredients to be released in an environment where they will not significantly degrade, and therefore can be absorbed.

It is a further aspect of the present invention to provide an oral vaccine delivery system having an enteric coating that delivers the active ingredient (the immunogen), without significant degradation, to the small intestine where the active ingredient can interact with the mucosal immune system and the lymphatic immune system. The delivery system of the present invention enables the vaccine to reach its target faster, to trigger a faster immune response, and to shorten the duration of the side effects of the vaccine.

It is a further aspect of the present invention to provide an oral influenza vaccine delivery system having an enteric coating that delivers the active ingredient (the immunogen), without significant degradation, to the small intestine where the active ingredient can interact with the mucosal immune system and the lymphatic immune system.

Apart from vaccine delivery, a further aspect of the present invention is the provision of an oral delivery system for many other active pharmaceutical compounds that can be absorbed from the digestive tract downstream of the stomach. Suitable payloads include insulin, any live or dead viral vaccines, enzymes and vitamins, including vitamin B12.

According to a preferred embodiment, the invention includes an inner pharmaceutical preparation fully enclosed in an outer enteric shell or coating. The outer shell consists of multiple solid shell segments joined together by a binder which also acts as a waterproof sealant for the gaps between the segments. The solid segments can be of various shapes and thicknesses.

In a preferred embodiment, the outer shell is of the typical ovoidal shape of a capsule, and is assembled from four segments: two hollow cylindrical segments and two segments shaped like end-caps. One annular strip of sealant connects the two cylindrical segments end to end to form the central hollow part of the capsule, and two more annular strips of sealant connect the two end-caps to the central part, fully enclosing an inner space where the pharmaceutical preparation is to be placed.

In other embodiments, the segments can be of various other shapes (hemispherical, strips, fibers, flakes, rods, wedges, scales, etc) and can be held together with other segments in a variety of ways (abutting on the edges, interwoven, interlocking, partly overlapping, etc). The binder-sealant can be positioned to seal the gaps between segments in a variety of ways: as a surface strip or bead, intra-joint bead or filler, inner or outer coating film, etc. The binder-sealant can either act as a sealant only (imparting liquid-tightness to the spaces between segments), or it can act both as a binder (mechanically fastening the segments together) and as a sealant. In a preferred embodiment, the segments are not mechanically or otherwise self-interlocking, so that, when the binder-sealant is dissolved or digested, the segments move apart, destroying the liquid-tight, multi-segment shell structure and releasing the inner contents.

In a further preferred embodiment, the segments of the outer shell are made of a suitable film or plate forming material that is liquid-proof and insoluble in a typical stomach environment (acid pH, presence of stomach enzymes, etc). In a further preferred embodiment, derivatives of cellulose are the choice material for the outer shell, but any other suitable material can be used that is impervious to stomach enzymes and insoluble at a pH lower than 5.5, or alternatively insoluble at a pH lower than 6.

In a further preferred embodiment, the binder consists of a suitable material that exhibits good adhesion to the segment material, and is liquid-proof and insoluble in a typical stomach environment (acid pH, presence of stomach enzymes, etc) but that is further soluble at a pH greater than 6 or under typical enzymatic environments such as that found in the small intestine.

In a further preferred embodiment, compositions containing fatty acids or mixtures of fatty acids are preferentially used as binder-sealer, with stearic acid as the preferred material. Any other suitable material can be used that that is easily degraded by the typical enzymes present in the small intestine or that dissolves at a pH above 7, or alternatively that dissolves at a pH above 6. Further fine point adjustments as to the precise intestinal locus of capsule disintegration are possible on the basis of a judicious selection of binders with different enzymatic and pH labilities.

In a preferred embodiment, the pharmaceutical preparation enclosed in the enteric shell is an acid labile pharmaceutical compound that would be degraded if exposed to the acid stomach environment. Representative examples of pharmaceutical compounds that can be used with preferred embodiments of this invention are: insulin, vaccines, enzymes and vitamins, including vitamin B12. In the case of insulin, the enteric coated capsule is taken approximately half an hour before eating.

In a further preferred embodiment, the pharmaceutical preparation enclosed in the enteric shell is an oral vaccine that needs to be delivered, without significant degradation, to the small intestine, where it can interact with the mucosal immune system and the lymphatic immune system. Typically, such vaccines contain as the immunogenic component (antigen) a suitable peptide or a protein fragment.

Taking into account that enzymes normally present in the small intestine environment can easily attack and degrade proteins and peptides, enzyme inhibitors are added to such oral vaccine preparations in a preferred embodiment, together with various other optional excipients (e.g. pH adjusters, permeation enhancers, mucoadhesives, adjuvants, micro-encapsulation additives, etc.).

In a further preferred embodiment, the oral vaccine enclosed in the enteric shell described by this invention is an oral influenza vaccine.

BRIEF DESCRIPTION OF THE DRAWINGS

Other aspects and advantages of the invention will become apparent upon reading the detailed description and upon referring to the drawings in which.

DETAILED DESCRIPTION OF PREFERRED EMBODIMENTS

Before explaining the present invention in detail, it is to be understood that the invention is not limited to the preferred embodiments contained herein. The invention is capable of other embodiments and of being practiced or carried out in a variety of ways. It is to be understood that the phraseology and terminology employed herein are for the purpose of description and not of limitation.

Figure 1:
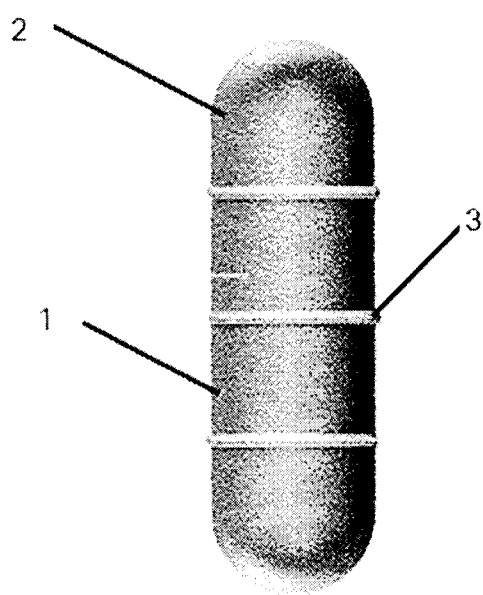
FIG. 1 shows a simplified drawing of a preferred embodiment of the invention, comprising an outer shell in the typical shape of a capsule, assembled from four segments: two cylindrical segments (1) and two segments shaped like end-caps (2). One annular strip of sealant (3) connects the two cylindrical segments end to end, to form the central hollow part of the capsule, and two more annular strips of sealant connect the two end-caps to the central part, fully enclosing an inner space where the pharmaceutical preparation is to be placed.
Figure 2:
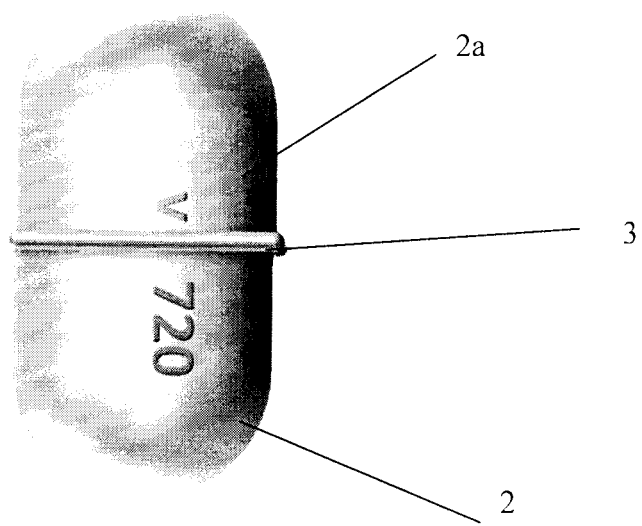
FIG. 2 shows a simplified drawing of an alternative preferred embodiment, where the outer shell is assembled from two half shells (2) and (2a) joined with an annular strip of sealant (3).

A preferred embodiment of the invention is generally illustrated in FIG. 1. The outer shell has the typical shape of a capsule, assembled from four segments: two cylindrical segments and two segments shaped like end-caps. In the preferred embodiment, the shell segments are made of derivatives of cellulose, but any other film or plate forming material that is compatible with the capsule's payload and is liquid-proof and insoluble in a typical stomach environment (low pH, presence of stomach enzymes, etc.) can be used. It is not necessary for such material to dissolve in the intestine; as long as the segments do not have sharp edges when the capsule breaks apart, they can be made of any suitable inert material which will end up eliminated in stools.

In the preferred embodiment of the invention shown in FIG. 1, strips of sealant connect the four segments to form a liquid-proof enclosure with a hollow inner space where the pharmaceutical preparation is placed. In the preferred embodiment, compositions based on stearic acid are used for binding and sealing the segments together. Stearic acid is a waxy substance with a melting point higher than normal body temperature, and impervious to the typical stomach environment. However, the strips of stearic acid binding the segments together are easily dissolved by bile and by pancreatic enzymes typically secreted in the small intestines, resulting in the destruction of the liquid-proof capsule enclosure and in the delivery of the payload to the intestinal lumen. Any other suitable sealant material that is easily degraded by the typical enzymes present in the small intestine or that dissolves at a pH above 7, or alternatively that dissolves at a pH above 6, can nonetheless be used as sealant instead of stearic acid.

To enhance the selectivity of the enteric release and to prevent unintended premature disintegration of the capsule in the stomach, other embodiments of the present invention may further employ one or more additional layers of coatings, to impart increased chemical and/or mechanical resistance to the capsule for the duration of its residence in the stomach. Various sugars, such as galactose, can be used for this purpose, however, any suitable coating or combination of enteric and non-enteric coatings can be used in conjunction with the present invention.

In a preferred embodiment, the pharmaceutical preparation enclosed in the enteric shell is an acid-labile pharmaceutical compound that would be degraded if exposed to the acid stomach environment. Representative examples of pharmaceutical compounds that can be used with preferred embodiments of this invention are, without limitation: insulin, vaccines, enzymes and vitamins, including vitamin B12.

A person skilled in the art would be able to ascertain the suitability of any combination of payload, shell material and sealant material based on known information pertaining to chemical and physical compatibility. A person skilled in the art would also be able to ascertain the limitations that various embodiments of this invention may face in specific situations. For example, an embodiment using stearic acid as sealer and binder would not make a suitable enteric delivery system if concomitant consumption of alcohol is expected, as the alcohol will dissolve or react with the stearic acid and prematurely disintegrate the capsule in the stomach.

What is claimed is:

1. A pharmaceutical composition comprising:
    an outer, liquid-tight shell comprising multiple segments of a plate-forming material, each segment having at least one open joining end, wherein said segments are joined together at respective joining ends only by a binding agent without being mechanically or otherwise self-interlocking, and wherein said segments have essentially the same dimension at the joining ends; and
    an inner preparation comprising an active substance and a suitable excipient.

2. The pharmaceutical composition of claim 1 wherein said plate-forming material is insoluble in pH environments in a stomach of a mammal.

3. The pharmaceutical composition of claim 1 wherein said plate-forming material is insoluble in a pH of less than about 5.5.

4. The pharmaceutical composition of claim 1 wherein said plate-forming material is insoluble in a pH of less than about 6.

5. The pharmaceutical composition of claim 1 wherein said plate-forming material comprises cellulose and its derivatives.

6. The pharmaceutical composition of claim 1 wherein said binding agent is insoluble in pH environments in a stomach of a mammal.

7. The pharmaceutical composition of claim 1 wherein said binding agent is insoluble in a pH of less than about 5.5.

8. The pharmaceutical composition of claim 1 wherein said binding agent is insoluble in a pH of less than about 6.

9. The pharmaceutical composition of claim 1 wherein said binding agent is soluble in a pH of about 7 or above.

10. The pharmaceutical composition of claim 1 wherein said binding agent is soluble in a pH of 6 or above.

11. The pharmaceutical composition of claim 1 wherein said binding agent is degradable by enzymatic secretions of a mammal's small-intestine.

12. The pharmaceutical composition of claim 1 wherein said binding agent consists of a fatty acid or mixtures containing the fatty acid.

13. The pharmaceutical composition of claim 12 wherein the fatty acid comprises stearic acid.

14. The pharmaceutical composition of claim 1 wherein said active substance comprises a pharmaceutically active substance.

15. The pharmaceutical composition of claim 14 wherein said pharmaceutically active substance comprises a vaccine preparation.

16. The pharmaceutical composition of claim 15 wherein said vaccine preparation comprises an influenza vaccine preparation.

17. The pharmaceutical composition of claim 14 wherein said pharmaceutically active substance comprises an insulin preparation.

18. The pharmaceutical composition of claim 1 wherein said active substance comprises at least one enzyme inhibitor.

19. The pharmaceutical composition of claim 1 wherein the outer, liquid-tight shell comprises four segments of a plate-forming material.

20. The use of the pharmaceutical composition of claim 1 in the treatment of disease comprising orally administering the pharmaceutical composition to a subject.

* * * * *